US012616791B2

(12) United States Patent
Jang

(10) Patent No.: US 12,616,791 B2
(45) Date of Patent: May 5, 2026

(54) DRUG INJECTION DEVICE

(71) Applicant: Won Jae Jang, Incheon (KR)

(72) Inventor: Won Jae Jang, Incheon (KR)

( * ) Notice: Subject to any disclaimer, the term of this patent is extended or adjusted under 35 U.S.C. 154(b) by 0 days.

(21) Appl. No.: 18/880,325

(22) PCT Filed: Jun. 30, 2023

(86) PCT No.: PCT/KR2023/009239
§ 371 (c)(1),
(2) Date: Dec. 31, 2024

(87) PCT Pub. No.: WO2024/005595
PCT Pub. Date: Jan. 4, 2024

(65) Prior Publication Data
US 2025/0161565 A1     May 22, 2025

(30) Foreign Application Priority Data
Jul. 1, 2022    (KR) ........................ 10-2022-0081261

(51) Int. Cl.
*A61M 5/168* (2006.01)
*A61M 5/142* (2006.01)
*A61M 5/315* (2006.01)
(52) U.S. Cl.
CPC ...... *A61M 5/1684* (2013.01); *A61M 5/14244* (2013.01); *A61M 5/16877* (2013.01); *A61M 5/31536* (2013.01); *A61M 5/31558* (2013.01); *A61M 5/31575* (2013.01); *A61M 2005/14208* (2013.01); *A61M 2005/3152* (2013.01); *A61M 2205/3379* (2013.01); *A61M 2205/3576* (2013.01)

(58) Field of Classification Search
CPC ........... A61M 5/1684; A61M 5/14244; A61M 5/16877; A61M 5/31536; A61M 5/31553; A61M 5/31558; A61M 5/3156; A61M 5/31568; A61M 5/31575; A61M 5/31583; A61M 2005/14208; A61M 2005/3152; A61M 2205/3379
See application file for complete search history.

(56) References Cited

U.S. PATENT DOCUMENTS

2021/0213205 A1 * 7/2021 Karlsson ................. A61M 5/24

FOREIGN PATENT DOCUMENTS

CN        110624160 A  * 12/2019
WO        WO-8302231 A1 * 7/1983

* cited by examiner

*Primary Examiner* — Michael J Tsai
*Assistant Examiner* — Forrest Blake Dipert
(74) *Attorney, Agent, or Firm* — IPLA P.A.

(57) ABSTRACT

A disclosed drug injection device includes: a case having a drug container located therein at one side; and a discharge amount adjustment module that is provided at the other side inside the case and, while rotating by a set angle only in one direction, adjusts a discharge amount of a drug stored in the drug container while speed is reduced by a speed reduction unit consisting of a combination of gears; a rotation amount detection module that detects a rotation value of the speed reduction unit and transmits detected data to a control device; and a locking module for locking to restrict rotation of the speed reduction unit when the rotation value detected by the rotation amount detection module reaches a set value.

2 Claims, 8 Drawing Sheets

100: 102,104,106,108
118: 1180,1190,1200
300: 310,320,330

(a)　　　　　　　　　(b)

(a)

(b)

(a)

(b)

(a)

(b)

DRUG INJECTION DEVICE

TECHNICAL FIELD

The present invention relates to a drug injection device, and more particularly to a device for manually subcutaneously injecting a drug, such as insulin, while being portable.

BACKGROUND ART

In general, a drug injection device, which is used to inject a drug into a patient's body, is one of the active treatment means and is used by medical professionals such as doctors or nurses, but in most cases, the drug injection device is used by ordinary people, such as patients or guardians.

Technology related to the drug injection device has been proposed in Korean Registered Utility Model No. 0486792.

However, Patent Document 1 has problems such as pain and exposure of the medical history of patients with underlying diseases due to frequent drug injection for a long period of time, limited places for administration, over-injection, and difficulty in fine adjustment.

In addition, other conventional patch-type drug injection devices have various problems such as "skin rash", "blockage", "removal upon further injection", "drug residual amount", "size" and "weight" of insulin pumps, and "price" and "maintenance cost", and insulin pens have problems such as "hypoglycemia in case of abnormal injection" and "skin pain in case of additional injection", and a solution is required to overcome the above problems.

(Patent Document 1) Korean Registered Utility Model No. 0486792 (2018.06.25)

Technical Problem

The present invention has been made in view of the above conventional problems, and it is an object of the present invention to provide a drug injection device capable of solving the problems of pain caused by frequent drug injection and abnormality of fine adjustment injection.

It is another object of the present invention to provide a drug injection device capable of solving problems of patch-type drug injection devices, such as "skin rash", "blockage", "removal upon further injection", "drug residual amount", "size" and "weight" of insulin pumps, and "price" and "maintenance cost", and problems of insulin pens, such as "hypoglycemia in case of abnormal injection" and "skin pain in case of additional injection".

Technical Solution

A drug injection device according to the present invention to accomplish the above objects includes a case having a drug container located on one side therein, a discharge amount adjustment module provided on the other side in the case, the discharge amount adjustment module being configured to adjust the discharge amount of a drug stored in the drug container in a state of being decelerated by a deceleration unit including a combination of gears while being rotated by a set angle only in one direction, a rotation amount detection module configured to detect the rotation value of the deceleration unit and to transmit detected data to a controller, and a locking module configured to lock the deceleration unit in order to limit rotation of the deceleration unit when the rotation value detected by the rotation amount detection module reaches a set value.

The discharge amount adjustment module may include a dial spring having a first fastening hole formed in the center thereof such that a fixed shaft is coupled to the first fastening hole, spring arms formed radially on an outer circumferential surface thereof, and a catching protrusion formed at each of ends of the spring arms, a dial configured to be rotated in a state in which a part of the dial is exposed through an opening of the case, the dial being provided with a coupling recess configured to allow the dial spring to be coupled thereto while having a second fastening hole formed in the center thereof and unidirectional teeth radially formed on an inner circumferential surface of the coupling recess, and a deceleration unit coupled to the dial so as to be interlocked therewith, the deceleration unit being configured to discharge a very small amount of the drug stored in the drug container while performing deceleration by multistage connection upon rotation of the dial.

The unidirectional teeth may be formed with alternating inclined and vertical surfaces such that, when the inclined surface contacts the catching protrusion of the dial spring, the spring arms are compressed to rotate the dial, and when the vertical surface contacts the catching protrusion of the dial spring, the spring arms are not compressed to prevent rotation of the dial.

The deceleration unit may include a power gear interlocked with the dial upon rotation of the dial, a lock gear engaged with one side of the power gear, the locking gear having an auxiliary gear formed at an end thereof, a sub gear engaged with the other side of the power gear, a rod gear engaged with the sub gear, and a screw helically engaged with a helical groove of the rod gear, the screw being configured to move an airtight portion provided in the drug container upon rotation of the rod gear.

The rotation amount detection module may include a magnetic body inserted into an end of a power gear of the deceleration unit so as to be rotated upon operation of the discharge amount adjustment module and a sensor configured to detect the rotation value of the magnetic body and to transmit detected data to the controller.

The locking module may include an upper bracket provided in a bent state, a lower bracket having one end extending through a lower part of a vertical portion of the upper bracket and a gear stopper configured to stop rotation of a lock gear of the deceleration unit provided at the other end, a magnet provided at a lower part of the lower bracket, and an electromagnet fixed to a lower part of a horizontal portion of the upper bracket, the electromagnet being magnetized by the flow of current, the electromagnet being configured to couple or separate the gear stopper to or from the lock gear of the deceleration unit according to polarity conversion.

The controller may set the rotation value of a dial of the discharge amount adjustment module, and may perform control such that rotation of the dial is stopped when the dial is rotated by the rotation value.

Advantageous Effects

According to the present invention, a drug injection dose may be monitored by a sensor through an application in a mobile phone or a dedicated controller, a manual dial is driven to inject a solution after the drug injection dose is set in the application, and when the set dose is reached, an internal locking module is operated to stop the operation of the dial, whereby it is possible to easily control the drug injection dose.

DETAILED DESCRIPTION OF THE INVENTION

Figure 1:
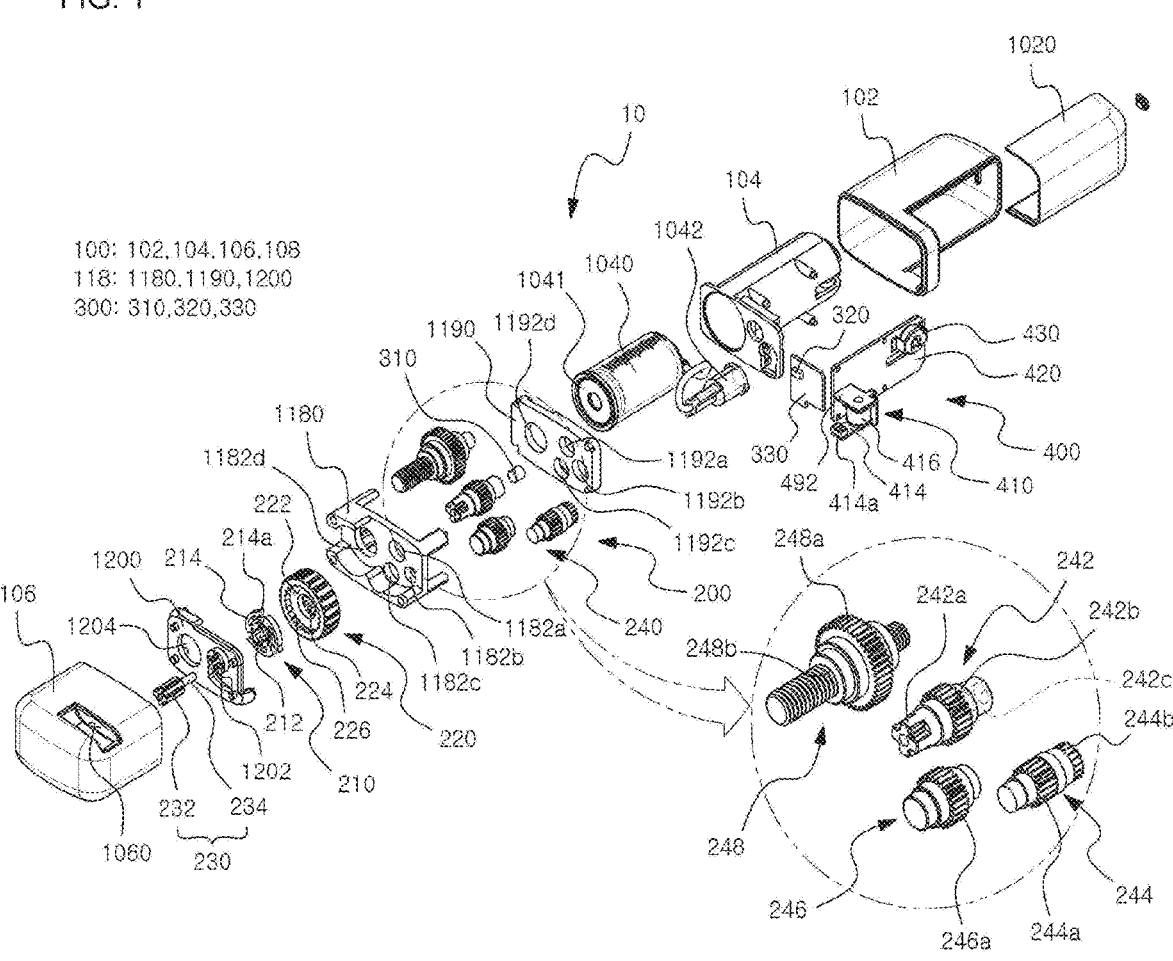
FIG. 1 is an exploded perspective view showing a drug injection device according to the present invention.

The above objects, features, and other advantages of the present invention will become more apparent by describing a preferred embodiment of the present invention in detail with reference to the accompanying drawings. Hereinafter, a drug injection device according to an embodiment of the present invention will be described in detail with reference to the accompanying drawings.

Referring to FIGS. 1 to 9, a drug injection device 10 according to an embodiment of the present invention includes a case 100, a discharge amount adjustment module 200, a rotation amount detection module 300, and a locking module 400, and is a device for discharging a very small amount of a drug stored in a drug container 1040 through a catheter 1042 connected to a discharge port of the drug container 1040.

At this time, although not shown in the drawings, the drug injection device 10 according to the present invention is capable of replacing a drug by dose as needed. That is, the capacity of the drug container 1040 may be adjusted by replacing the discharge amount adjustment module 200, which is a driving part. In this case, the length of a screw 250 and the capacity of the drug container 1040 are changed in the discharge amount adjustment module 200 located in a cap case 106.

Figure 2:
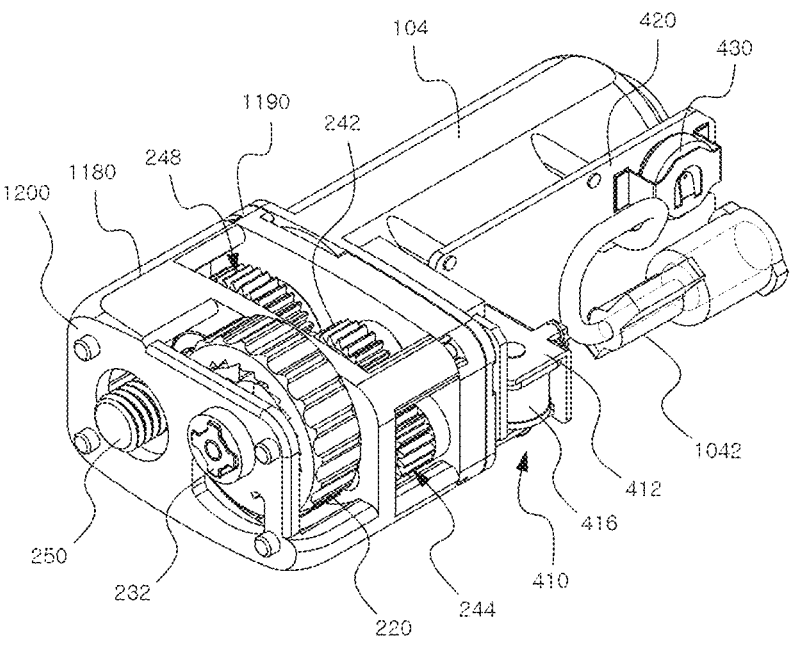
FIGS. 2 and 3 are separated perspective views showing a body case and a cap case in the drug injection device according to the present invention, respectively.
Figure 3:
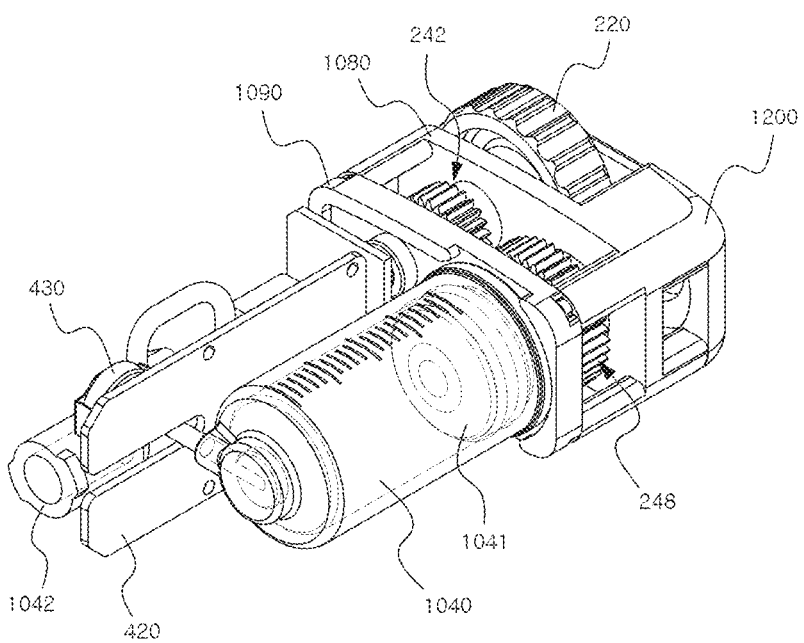
Figure 4:
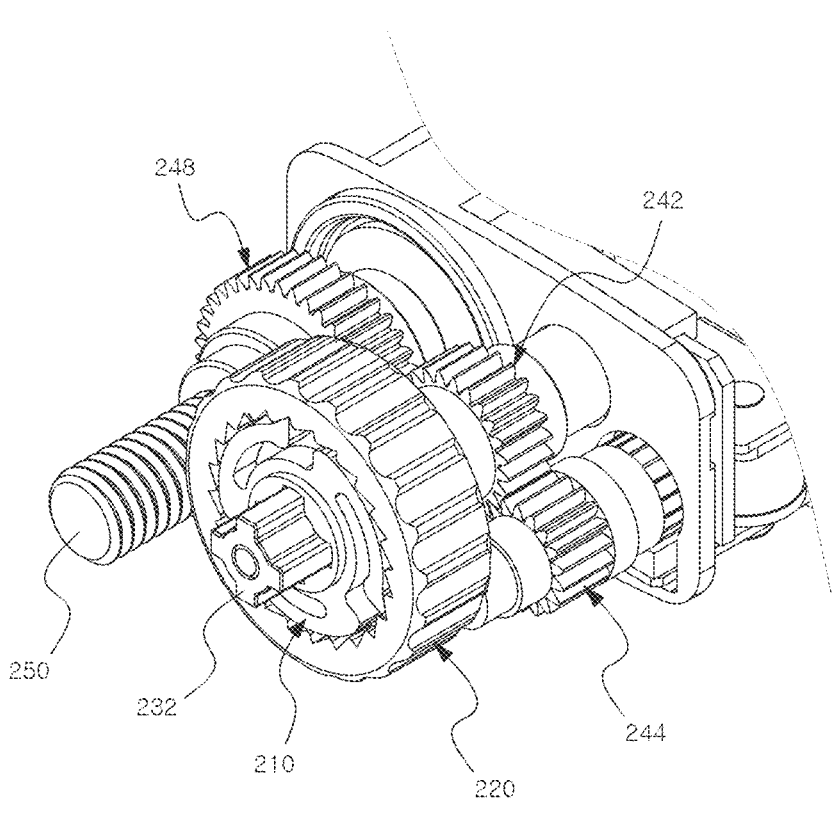
FIG. 4 is a perspective view showing a discharge amount adjustment module in the drug injection device according to the present invention.
Figure 5:
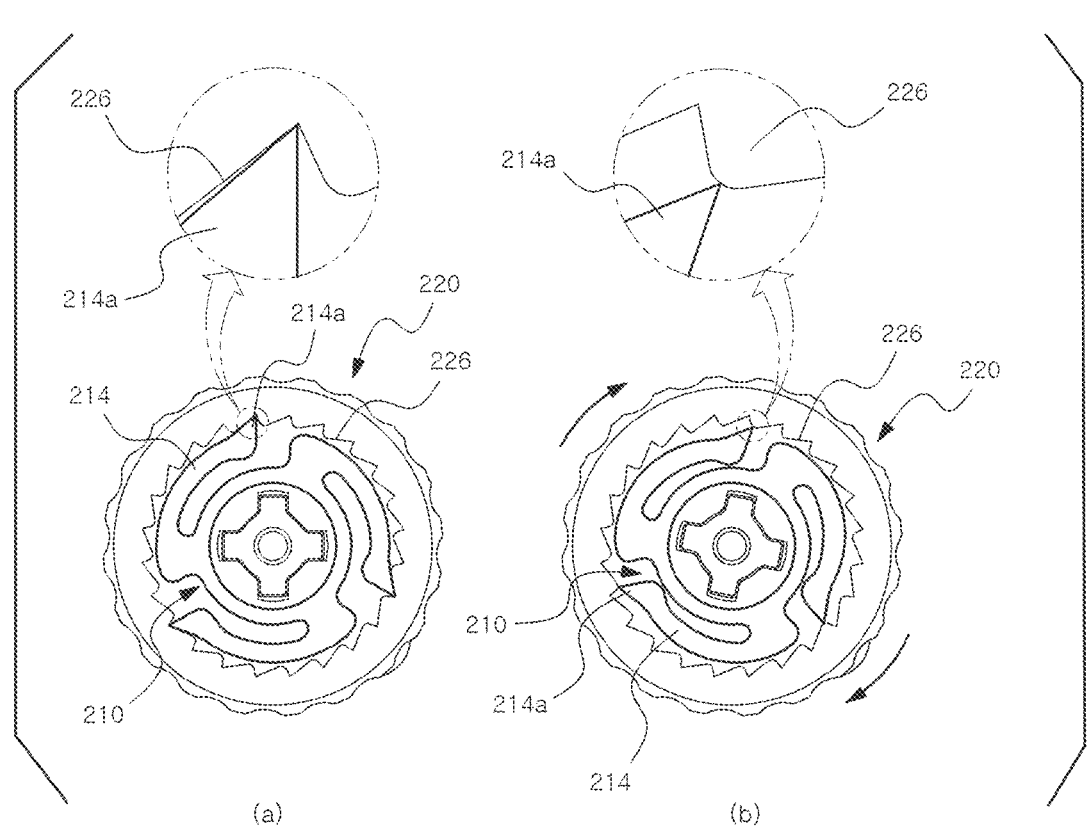
FIG. 5 is a front view showing the state of a dial to which a dial spring is coupled in the drug injection device according to the present invention before and after rotation.
Figure 6:
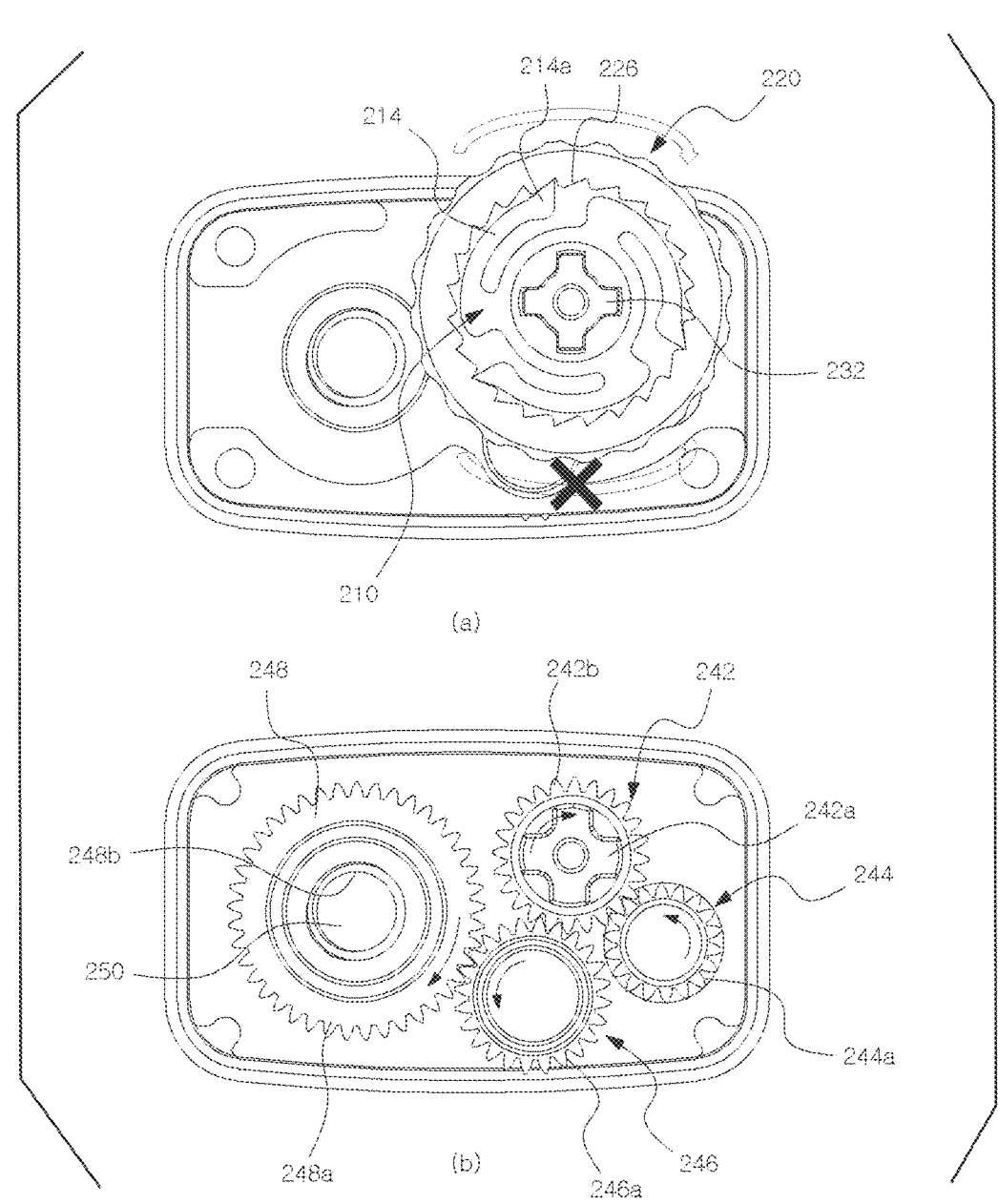
FIG. 6 is a front view of the dial with the dial spring is coupled in the drug injection device according to the present invention and a front view of a deceleration unit.

As shown in FIGS. 1 to 3, the case 100 includes a body case 102 having an opening formed on one side thereof and a catheter cover 1020 provided on the other side of a side surface thereof, an inner case 104 inserted into the body case 102 and having the drug container 1040 located therein, and a cap case 106 connected to the front of the body case 102.

At this time, the cap case 106 is provided with an opening 1060, through which a part of a dial 220 of the discharge amount adjustment module 200 is exposed, and a user artificially rotates the end of the dial 220 exposed through the opening 1060.

A bracket 118 located in the cap case 106 to support a fixed shaft 230 and a deceleration unit 240 of the discharge amount adjustment module 200 is fixed to the front of the body case 102.

The bracket 118 includes a first gear bracket 1180, a second gear bracket 1190, and a third gear bracket 1200.

The first gear bracket 1180 has a first support hole to a fourth support hole 1182a, 1182b, 1182c, and 1182d formed in a lateral direction so as to rotatably support front ends of a power gear 242, a lock gear 244, a sub gear 246, and a rod gear 248 of the deceleration unit 240, respectively.

The second gear bracket 1190 is located at the rear of the first gear bracket 1180 in a state of being spaced apart therefrom, and has a fifth support hole to an eighth support hole 1192a, 1192b, 1192c, and 1189d formed in the lateral direction so as to rotatably support rear ends of the power gear 242, the lock gear 244, the sub gear 246, and the rod gear 248 of the deceleration unit 240, respectively.

At this time, a surface of the lock gear 244 between a first gear 244a and an auxiliary gear 244b is supported in the sixth support hole 1192b.

The third gear bracket 1200 is located in front of the first gear bracket 1180, and has a ninth support hole 1202 formed in the lateral direction so as to concentric with the first support hole 1182a of the first gear bracket 1180.

At this time, the ninth support hole 1202 is provided with a recess corresponding to a protrusion 232 provided at a front end of the fixed shaft 230.

As shown in FIGS. 1 to 6, the discharge amount adjustment module 200 is provided in the cap case 106 while being located in front of the body case 102 to adjust the discharge amount of the drug stored in the drug container 1040 in a state of being decelerated by a deceleration unit 240, which is constituted by a combination of gears, while being rotated by a set angle only in one direction, and includes a dial spring 210, a dial 220, a fixed shaft 230, and a deceleration unit 240.

The dial spring 210 has a first fastening hole 212 formed crosswise in the center thereof so as to correspond to the ninth support hole 1202 such that rotation prevented when the protrusion 232 of the fixed shaft 230 is coupled to the ninth support hole 1202 and the first fastening hole 212, spring arms 214 are formed radially on an outer circumferential surface of the dial spring, and a catching protrusion 214a is formed at each of ends of the spring arms 214.

At this time, the spring arms 214 extend radially at three points so as to be equidistantly spaced from each other at an outer surface of the first fastening hole 212, and extend from the extended ends in an arc shape, whereby the spring arms 214 have elastic force when the ends are pressed and released, and the catching protrusion 214a is configured to be caught by teeth 226 on an outer surface of each end.

Consequently, the dial spring 210 causes the spring arms 214 to support the unidirectional teeth 226 formed on the inside of the dial 220 such that the dial 220 rotates only in one direction.

The dial 220 is located such that a part of the dial is exposed through the opening 1060 of the cap case 106, and has a coupling recess 222 formed at a front center for coupling with the dial spring 210 and a second fastening hole 224, which is crosswise shaped, laterally formed through the center of the coupling recess 222 for coupling with a coupling protrusion 242a of the power gear 242.

Furthermore, the unidirectional teeth 226 are formed on an inner circumferential surface of the coupling recess 222. The teeth 226 are formed with alternating inclined and vertical surfaces such that, when the inclined surface contacts the catching protrusion 214a of the dial spring 210, the spring arms 214 are compressed to rotate the dial 220, and when the vertical surface contacts the catching protrusion 214a of the dial spring 210, the spring arms 214 are not compressed to prevent rotation of the dial 220. Consequently, the dial 220 is configured to have a structure in which reverse rotation the dial is prevented such that the dial can rotate only in one direction.

As such, the dial 220 may be rotated at predetermined intervals to facilitate control of the solution injection capacity.

That is, when the dial 220 is rotated, the spring arms 214 of the dial spring 210 catch the teeth 226 one step at a time such that the rotation of the dial 220 is constant, whereby the solution is injected in a constant amount according to the amount of rotation of the dial 220.

When the dial 220 is rotated, the power gear 242, the sub gear 246, and the rod gear 248 of the deceleration unit 240 perform deceleration in three stages to slow down the screw 250 engaged with the rod gear 248, thereby releasing a very small amount of the solution in the drug container 1040.

The fixed shaft 230 has a cross-shaped protrusion 232 formed such that one end thereof is irregularly coupled to the ninth support hole 1202 of the third gear bracket 1200 and an extension shaft 234 extending from the other end of the protrusion 232 so as to be coupled to a hole formed in the front end of the power gear 2420 of the deceleration unit 240.

The deceleration portion 240 is coupled to the dial 220 so as to be interlocked therewith to discharge a very small amount of the drug stored in the drug container 1040 while performing deceleration by multistage connection upon rotation of the dial 220, and includes a power gear 242, a lock gear 244, a sub gear 246, a rod gear 248, and a screw 250.

At this time, the power gear 242, the sub gear 246, and the rod gear 248, except for the lock gear 244, cause the dial 220 to be decelerated upon rotation of the dial, and finally cause the screw 250 to advance at a low speed.

Both ends of the power gear 242 are rotatably supported in the first support hole 1182a of the first gear bracket 1180 and the fifth support hole 1192a of the second gear bracket 1190, a cross-shaped coupling protrusion 242a is formed at the front end of the power gear extending through the first support hole 1182a, a first gear 242b is formed at the rear of the coupling protrusion 242a, and a coupling recess 242c, to which a magnetic body 310 of the rotation amount detection module 300 is coupled, is formed at the rear of the first gear 242b so as to be depressed.

The coupling protrusion 242a is formed in a shape corresponding to the second fastening hole 224 of the dial 220 such that, when coupled, the power gear 242 is interlocked when the dial 220 is rotated, and the first fastening hole 212 of the dial spring 210 is not interlocked because the protrusion 232 of the fixed shaft 230 is coupled thereto.

Both ends of the lock gear 244 are rotatably supported in the second support hole 1182b of the first gear bracket 1180 and the sixth support hole 1192b of the second gear bracket 1190, and is provided with a first gear 244a configured to engage with one side of the first gear 242b of the power gear 242 and an auxiliary gear 244b provided at the rear extending through the sixth support hole 1192b of the second gear bracket 1190.

Here, the lock gear 244 prevents further rotation of the auxiliary gear 244b by the locking module 400 when the power gear 242 reaches a set rotation value, ultimately stopping the rotation of the dial 220.

Both ends of the sub gear 246 are rotatably supported in the third support hole 1182c of the first gear bracket 1180 and the seventh support hole 1192c of the second gear bracket 1190, and is provided with a first gear 246a configured to engage with the other side of the first gear 242b of the power gear 242.

Both ends of the rod gear 248 are rotatably supported in the fourth support hole 1182d of the first gear bracket 1180 and the eighth support hole 1192d of the second gear bracket 1190, and is provided with a first gear 248a configured to engage with the first gear 246a of the sub gear 246.

Furthermore, the rod gear 248 has a helical groove 248b formed in the center thereof so as to be helically engaged with the screw 250. Consequently, the screw 250 advances when the rod gear 248 is rotated.

Figure 7:
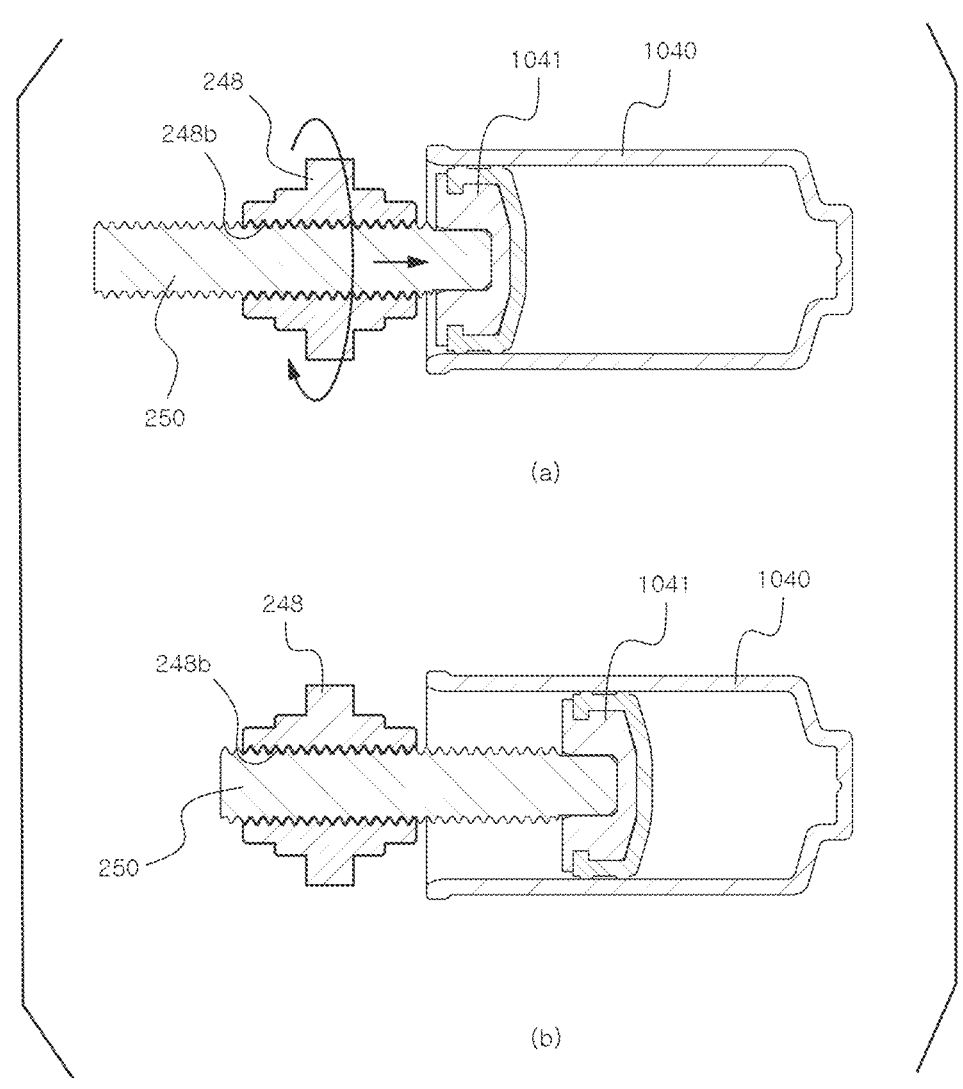
FIG. 7 is a sectional view showing the state in which an airtight portion of a drug container is moved by rotation of a screw in the drug injection device according to the present invention.

As shown in FIG. 7, the screw 250 is helically engaged with the helical groove 248b of the rod gear 248, and an airtight portion 1041 provided in the drug container 1040 is connected to the end of the screw such that the airtight portion 1041 is moved upon rotation of the rod gear 248.

Figure 8:
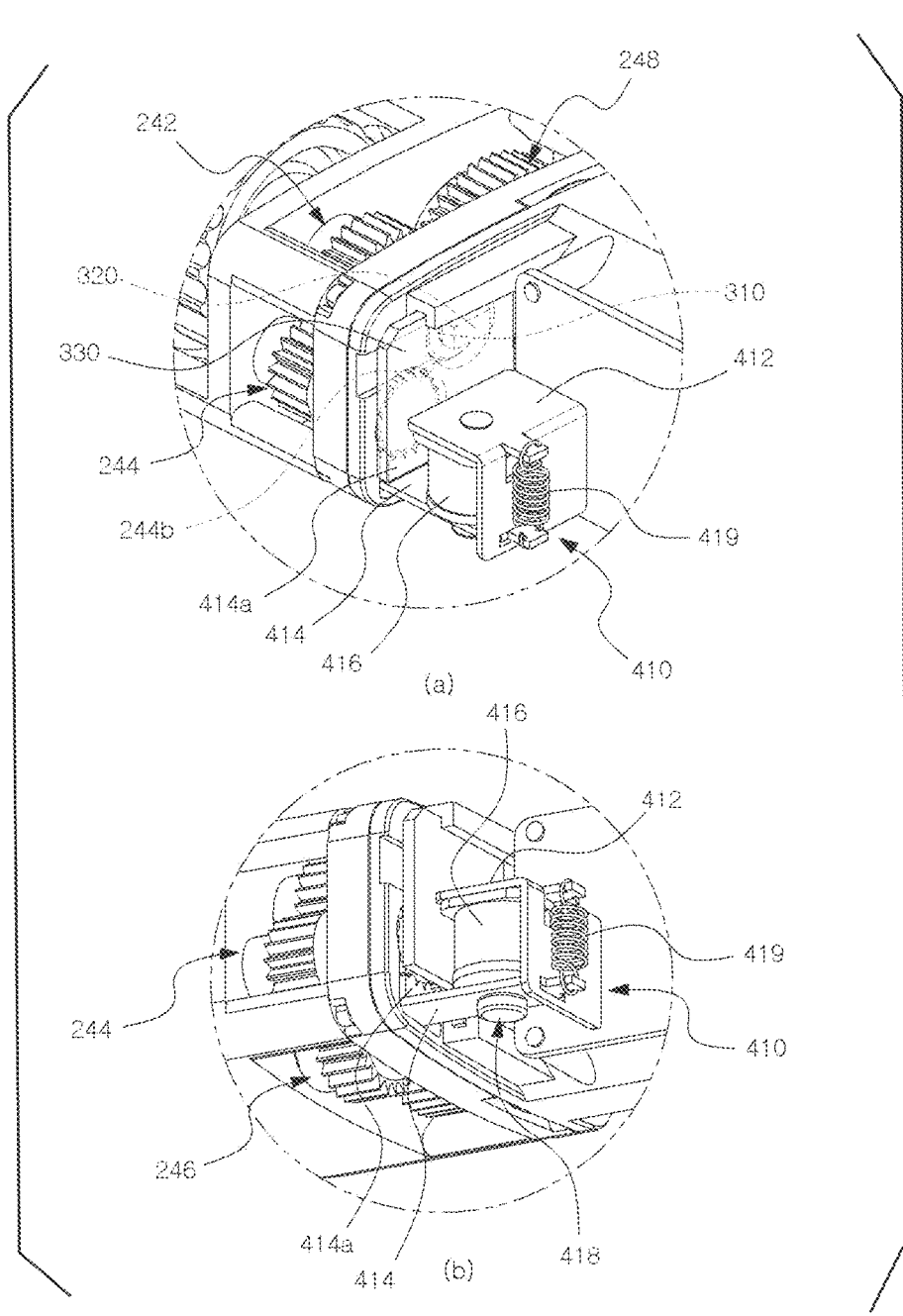
FIG. 8 is a perspective view showing a locking unit in the drug injection device according to the present invention.
Figure 9:
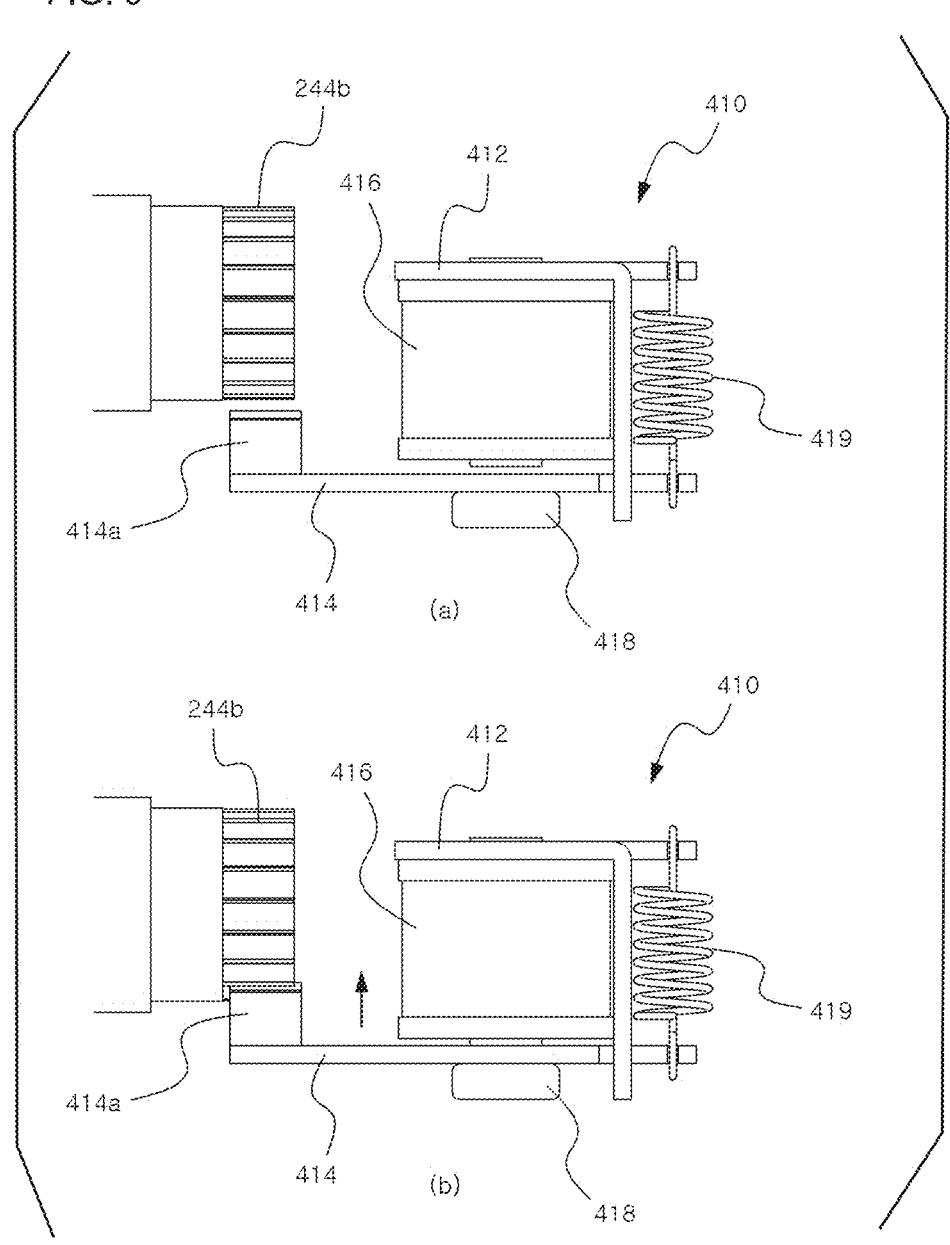
FIG. 9 is a side view showing an operating state of the locking unit in the drug injection device according to the present invention.

As shown in FIGS. 1 and 8, the rotation amount detection module 300 functions to detect the manual rotation amount of the dial 220. The rotation amount detection module detects the rotation value of the deceleration unit 240 interlocked with the dial 220, and transmits the detected data to a controller (not shown), and includes a magnetic body 310 and a sensor 320.

The magnetic body 310 is a magnet coupled to the coupling recess 242c of the power gear 242.

The sensor 320, which is a Hall sensor, senses the rotation of the magnetic body 310. At this time, the sensor 320 is supported by a sensor PCB 330.

As such, the rotation amount detection module 300 has a structure in which the power gear 242 and the magnetic body 310 located at the rear end of the power gear 242 are regularly rotated together when the dial 220 is rotated, the sensor 320 detects the rotation value of the magnetic body 310, the detected data is transmitted to the controller via the sensor PCB 330 and a main PCB 420, and the injection amount of solution by the manual rotation of the dial 220 is managed by an application of the controller.

As shown in FIGS. 1 to 3, 8, and 9, the locking module 400 basically locks the lock gear 244, and includes a locking unit 410 and a main PCB 420 configured to lock the lock gear 244 of the deceleration unit 240 so as not to be rotated when the rotation value detected by the rotation amount detection module 300 reaches a set value, to release the locked state when an operation signal is received from the application of the controller, and to re-lock the lock gear 244 at the set rotation value when rotation of the dial 220 is detected as the dial 220 becomes operable.

The locking unit 410 includes an upper bracket 412, a lower bracket 414, an electromagnet 416, a magnet 418, and a spring 419.

The upper bracket 412 is formed in a "¬" shape on the side, the boundary of a horizontal portion and a vertical portion is incised in a "[" shape so as to be located in the same plane as the horizontal portion, and a through hole through which one end of the lower bracket 414 extends is formed in a lower end of the horizontal portion.

The lower bracket 414 is provided parallel to the horizontal portion of the upper bracket 412, and one end of the lower bracket is disposed so as to extend through a through-hole formed in the lower end of the horizontal portion of the upper bracket 412.

The lower bracket 414 is provided with a gear stopper 414a having gear teeth formed on an upper part of the other end thereof such that the lock gear 244 is rotated when engaged with the auxiliary gear 244b of the lock gear 244 the lock gear 244 is rotated when disengaged from the auxiliary gear 244b of the lock gear 244.

The electromagnet 416 is fixed to a lower part of the horizontal portion of the upper bracket 412 and is magnetized by the flow of current and, depending on the polarity conversion, upwardly moves the lower bracket 414 by attraction with the magnet 418 provided at the lower part of the lower bracket 414, causing the gear stopper 414a to be coupled to the auxiliary gear 244b of the lock gear 244, or depending on the polarity conversion, downwardly moves the lower bracket 414 by repulsion with the magnet 418 provided at the lower part of the lower bracket 414 in accordance with the polarity conversion, causing the gear stopper 414a to be released from the auxiliary gear 244b of the lock gear 244.

Meanwhile, the electromagnet 416 is energized through a battery 430 provided in the main PCB 420.

The magnet 418 is provided at the lower part of the lower bracket 414 in line with the electromagnet 416 to generate attraction or repulsion depending on the change in polarity of the electromagnet 416.

The spring 419 is a compression spring configured such that both ends of the compression spring are supported by the end of the horizontal portion of the upper bracket 412 and one end of the lower bracket 414 extending through the vertical portion of the upper bracket 412, respectively.

At this time, the spring 419 moves the lower bracket 414 upward and downward in response to a change in the polarity of the electromagnet 416, and auxiliary causes the lower bracket 414 to be always moved upward in a direction toward the upper bracket 412 such that the gear stopper 414a remains engaged with the auxiliary gear 244b of the lock gear 244.

The operation of the drug injection device 10 according to the present invention will be described as follows.

First, the lower bracket 414 is moved upward by attraction between the electromagnet 416 and the magnet 418 provided at the lower part of the lower bracket 414 according to the polarity conversion of the electromagnet 416 provided at the locking module 400, whereby the gear stopper 414a is coupled to the auxiliary gear 244b of the lock gear 244, rotation of the power gear 242, the sub gear 246, and the rod gear 248 engaged with the non-rotatable auxiliary gear 244b are prevented by the auxiliary gear 244b, and the dial 220 fixed to the power gear 242 is in a non-rotatable state.

At this time, the application of the controller presets the rotation value of the dial 220 of the discharge amount adjustment module 200.

Subsequently, when an operation signal is transmitted from the application of the controller, the lower bracket 414 is moved downward by repulsion between the electromagnet 416 and the magnet 418 provided at the lower part of the lower bracket 414 according to the polarity conversion of the electromagnet 416, whereby the gear stopper 414a is separated from the auxiliary gear 244b of the lock gear 244.

Subsequently, when the dial 220 is rotated, the unidirectional teeth 226 formed on the inner circumferential surface of the coupling recess 222 of the dial 220 are supported by the catching protrusion 214a of the spring arm 214 provided at the dial spring 210, whereby rotation is performed only in one direction, which is a direction toward the inclined surface.

Subsequently, the dial 220 is rotated at intervals equal to the angle of the teeth 226 to rotate the power gear 242, the screw 250 helically engaged with the helical groove 248b of the rod gear 248 is advanced at a low speed due to deceleration by the power gear 242, the sub gear 246, and the rod gear 248, and the airtight portion 1041 provided at the front end of the screw 250 discharges a drug stored in the drug container 1040 through the catheter 1042 in a very small amount corresponding to the angle of rotation of the dial 220.

At this time, when the power gear 242 is rotated, the magnetic body 310 located at the rear end of the power gear 242 is also regularly rotated along therewith, and the rotation value of the magnetic body 310 is detected by the sensor 320 of the sensor PCB 330, and the detected data is transmitted to the controller via the main PCB 420 to control the injection amount of the solution by manual rotation of the dial 220 through the application of the controller.

Subsequently, since the rotation value of the dial 220 is set by the application of the controller, a patient rotates the dial 220 to inject the set amount of the drug, and when the dial 220 reaches the set rotation value based on the rotation value detected by the sensor 320, the locking module 400 is operated, whereby the gear stopper 414a of the lower bracket 414 is fixed to the auxiliary gear 244b of the lock gear 244 as the electromagnet 416 is magnetized, and therefore rotation of the dial 220 connected to the lock gear 244 is prevented.

While the embodiments of the present invention have been described above with reference to the accompanying drawings, it will be understood by those having ordinary skill in the art to which the present invention pertains that the present invention can be embodied in other specific forms without changing the technical ideas or essential features of the invention. It should therefore be understood that the embodiments described above are illustrative in all respects but not restrictive.

DESCRIPTION OF REFERENCE NUMERALS

10: Drug injection device
100: Case
1040: Drug container
200: Discharge amount adjustment module
210: Dial spring
220: Dial
230: Fixed shaft
240: Deceleration unit
300: Rotation amount detection module
310: Magnetic body
320: Sensor
400: Locking module
410: Locking unit

The invention claimed is:
1. A drug injection device comprising:
a case having a drug container located on one side therein;
a discharge amount adjustment module provided on a side of the case different from the side of the case the drug container is located on, and being rotated by a set angle only in one direction;
a rotation amount detection module configured to detect a rotation value of a deceleration unit and to transmit detected data to a controller; and
a locking module configured to lock the deceleration unit in order to limit rotation of the deceleration unit when the rotation value detected by the rotation amount detection module reaches a set value,
wherein the discharge amount adjustment module comprises:

a dial spring having a first fastening hole formed in a center thereof such that a fixed shaft is coupled to the first fastening hole, spring arms formed radially on an outer circumferential surface of the dial spring, and a catching protrusion formed at an end of each spring arm;

a dial configured to be rotated in a state in which a part of the dial is exposed through an opening of the case, wherein the part of the dial exposed through the opening of the case is configured to be directly manually rotated by a user, wherein when the dial is directly manually rotated by the user the drug in the drug container is discharged;

the dial being provided with a coupling recess coupling the dial spring to the dial while having a second fastening hole of the dial and unidirectional teeth radially formed on an inner circumferential surface of the coupling recess; and the deceleration unit comprising a combination of gears and coupled to the dial so as to be interlocked therewith, the deceleration unit being configured to discharge some amount of the drug stored in the drug container while performing deceleration by multistage connection upon rotation of the dial, wherein the rotation amount detection module comprises:

a magnetic body inserted into an end of a power gear of the deceleration unit so as to be rotated upon operation of the discharge amount adjustment module; and a sensor configured to detect a rotation value of the magnetic body and to transmit detected data to the controller, wherein the locking module comprises:

an upper bracket provided in a bent state;

a lower bracket having one end extending through a lower part of a vertical portion of the upper bracket and a gear stopper with gear teeth configured to stop rotation of a lock gear of the deceleration unit provided at an end of the lower bracket different from the lower bracket's end which extends through the upper bracket, the lock gear having an auxiliary gear formed at an end thereof;

a magnet provided at a lower part of the lower bracket; and an electromagnet fixed to a lower part of a horizontal portion of the upper bracket, the electromagnet being magnetized by a flow of current, the electromagnet being configured to couple or separate the gear stopper to or from the lock gear of the deceleration unit according to polarity conversion; and a compression spring configured such that one end of the compression spring is supported by an end of the horizontal portion of the upper bracket vertically above the electromagnet and another end of the compression spring is supported by the end of the lower bracket extending through the vertical portion of the upper bracket, wherein the electromagnet and magnet are both disposed between the compression spring and the auxiliary gear in a direction parallel with the auxiliary gear's axis of rotation, wherein the controller sets a rotation value of the dial of the discharge amount adjustment module, and performs control of the gear stopper such that manual rotation of the dial is stopped when the dial is rotated by the rotation value which was set in the controller, wherein the unidirectional teeth are formed with alternating inclined and vertical surfaces such that, when the inclined surface contacts the catching protrusion of the dial spring, the spring arms are compressed to rotate the dial, and when the vertical surface contacts the catching protrusion of the dial spring, the spring arms are not compressed, wherein the drug in the drug container is discharged while the catching protrusion of the dial spring contacts the inclined surface from one end of the inclined surface to the other end of the inclined surface, wherein when the gear teeth of the gear stopper is engaged with the gear teeth of the auxiliary gear the dial cannot be rotated by the user and when the gear teeth of the gear stopper is disengaged from the gear teeth of the auxiliary gear the dial can be rotated by the user, and wherein the gear stopper is engaged with the auxiliary gear by moving vertically upward and the gear stopper is disengaged from the auxiliary gear by moving vertically downward.

2. The drug injection device according to claim 1, wherein the deceleration unit comprises:

the power gear interlocked with the dial upon rotation of the dial;

the lock gear engaged with one side of the power gear, a sub gear engaged with the power gear on a different side of the power gear than the side of the power gear the lock gear engages with;

a rod gear engaged with the sub gear; and a screw helically engaged with a helical groove of the rod gear, the screw being configured to move an airtight portion provided in the drug container upon rotation of the rod gear.

* * * * *